United States Patent [19]

Veit

[11] Patent Number: 4,540,525

[45] Date of Patent: Sep. 10, 1985

[54] METHOD FOR PRODUCING 1-NAPHTHOL-4-SULPHONIC ACID

[75] Inventor: Werner Veit, Langkampfen, Austria

[73] Assignee: Sandoz Ltd., Basel, Switzerland

[21] Appl. No.: 645,942

[22] Filed: Aug. 30, 1984

Related U.S. Application Data

[63] Continuation-in-part of Ser. No. 597,172, Apr. 5, 1984, abandoned.

[51] Int. Cl.³ .......................................... C07C 143/42
[52] U.S. Cl. ................................................ 260/512 C
[58] Field of Search .................................... 260/512 C

[56] References Cited

U.S. PATENT DOCUMENTS

| | | | |
|---|---|---|---|
| 1,452,481 | 4/1923 | Boddiley et al. | 260/512 C |
| 1,570,046 | 1/1926 | Crossley et al. | 260/512 C |
| 1,662,396 | 3/1928 | Parmelee | 260/512 C |
| 3,994,966 | 11/1976 | Hagedorn | 260/512 C |

Primary Examiner—Alan Siegel

[57] ABSTRACT

Disclosed is a method for producing 1-naphthol-4-sulphonic acid in free acid form and contaminated with less than 2% by weight of the isomeric 1-naphthol-2-sulphonic acid.

20 Claims, No Drawings

METHOD FOR PRODUCING 1-NAPHTHOL-4-SULPHONIC ACID

This application is a continuation-in-part of Application Ser. No. 597,172, filed Apr. 5, 1984 and now abandoned.

The present invention relates to a method for producing 1-naphthol-4-sulphonic acid, known as Nevile-Winther acid (NW acid), with a low content of the isomeric 1-naphthol-2-sulphonic acid.

It is known that sulphonation of 1-naphthol with sulphuric acid, oleum, sulphur trioxide or chlorosulphonic acid leads to mixtures of sulphonic acids, namely 1-naphthol-4-sulphonic acid, 1-naphthol-2-sulphonic acid, 1-naphthol-2,4-disulphonic acid and 1-naphthol-2,4,7-trisulphonic acid. To improve the yield of the monosulphonic acids, it has been proposed to carry out the sulphonation under conditions such that part of the starting 1-naphthol remains unsulphonated.

Alternatively, polysulphonation of 1-naphthol can be significantly reduced or practically avoided by using solvents which are inert under the reaction conditions, e.g. acetic acid, tetrachloroethane, benzene, nitrobenzene and other nitrated or halogenated organic solvents. Although the use of some of these solvents enables all the initial 1-naphthol to be sulphonated, the resulting sulphonation product is a mixture of isomeric monosulphonic acids.

The Nevile-Winther acid is a useful product, widely employed for organic synthesis. It is particularly used as a coupling component for the production of a great number of azo dyes. Therefore it is highly desirable to produce 1-naphthol-4-sulphonic acid as free as possible from the isomeric 1-naphthol-2-sulphonic acid obtained as by-product in the sulphonation of 1-naphthol, and also free from unsulphonated 1-naphthol, since both products also react as coupling components. Contamination with 1-naphthol-di- and -tri-sulphonic acids is less serious for this application, as they do not couple with diazonium salts.

Various attempts to improve the yield of 1-naphthol-4-sulphonic acid over 1-naphthol-2-sulphonic acid have been made, particularly by varying the reaction conditions, especially by operating at temperatures above 50° C.

However contamination of the 4-isomer by the 2-isomer is still too high and further purification steps are needed. The usual procedure to separate the 2-isomer from the 4-isomer is fractional salting out of an aqueous solution of the isomeric sulphonic acid mixture, based on the fact that the alkali or alkaline earth metal salts of the 2-isomer are less water-soluble than those of the 4-isomer. However, not only does the 2-isomer contamination in the finally purified 4-isomer still amount to 5 to 10% by weight but also the yield of the 4-isomer salt is significantly reduced by the elaborate purification steps. Furthermore, the salting out process requires high quantities of salt, thus polluting the waste water to an undesirable extent.

It has now been found that 1-naphthol-4-sulphonic acid in the free acid form having a very low content of 1-naphthol-2-sulphonic acid can be obtained directly without elaborate purification steps.

Accordingly, there is provided a method for producing 1-naphthol-4-sulphonic acid in free acid form contaminated with less than 2% by weight of 1-naphthol-2-sulphonic acid, by sulphonating 1-naphthol in a solvent which is substantially inert towards the sulphonating agent and in which 1-naphthol-4-sulphonic acid has a solubility at a temperature $>50°$ C. of from 0.01 to 5.0% by weight, which method comprises the step of separating the 1-naphthol-4-sulphonic acid from the reaction mixture by filtration at a temperature $>50°$ C. directly after completion of the sulphonation.

Suitable solvents for the sulphonation include aromatic monocyclic hydrocarbons which may be further nitrated or halogenated, e.g. benzene, toluene, xylene, nitrobenzene, nitrotoluene, mono-, di- or tri-chlorobenzenes, or halogenated aliphatic hydrocarbons, e.g. chloroform, trichloroethylene, 1,1,1- or 1,1,2-trichloroethane, tetrachloroethylene or 1,1,2,2-tetrachloroethane. Depending on the sulphonating conditions and on the sulphonating agent, some aromatic monocyclic hydrocarbons are not fully inert and may be partially sulphonated, e.g. an aromatic monocyclic hydrocarbon such as benzene, toluene or xylene. Preferred solvents are those which are fully inert towards the sulphonating agent, with the halogenated benzenes being more preferred and monochlorobenzene being most preferred.

The amount of solvent which may be used according to the invention, is generally from 2 to 20 times, preferably from 5 to 10 times, the amount of 1-naphthol, by weight.

By a solubility of 0.01 to 5.0% by weight is meant that 0.01 to 5.0 g of 1-naphthol-4-sulphonic acid are soluble in 100 g solvent at a temperature $>50°$ C., i.e. from 50° C. to the boiling point of the solvent.

Suitable sulphonating agents include sulphuric acid, oleum, sulphur trioxide and chlorosulphonic acid. Chlorosulphonic acid is the most preferred sulphonating agent. It can be fully consumed in the reaction, even if a slight excess is originally present (e.g. by formation of disulphonic acids or reaction with the solvent) and the only by-product is hydrogen chloride, which is evolved as a gas. Chlorosulphonic acid gives superior yields and purities than other sulphonating agents.

Chlorosulphonic acid is generally used in an excess up to 20% by weight of the stoichiometric amount. When a solvent inert towards the sulphonating agent is used, e.g. halogenated or nitrated hydrocarbons as indicated above, the sulphonation is carried out with the stoichiometric amount or a slight excess, e.g. up to 5% by weight of chlorosulphonic acid. When a solvent partially sensitive to the sulphonating conditions is used as reaction medium, chlorosulphonic acid is added in an excess from 5 to 20% by weight to achieve complete sulphonation of 1-naphthol.

Sulphonation with chlorosulphonic acid is conveniently performed by adding it slowly, e.g. dropwise, to the dissolved 1-naphthol, advantageously at a temperature from $-20°$ C. to 120° C. When a partially sensitive solvent is used for the reaction medium, the addition of the sulphonating agent is preferably effected at the lower end of this temperature range, e.g. from $-20°$ C. to $+20°$ C. If a fully inert solvent is used, the sulphonating agent is preferably added at a higher temperature, i.e. $>20°$ C. depending on the boiling point of the solvent used. When addition of the chlorosulphonic acid is complete, the reaction mixture is further heated at a temperature $>50°$ C., preferably at a temperature from 60° to 100° C., for 1 to 12 hours. If a solvent with a boiling point below the temperature ranges indicated above is used, the heating may be carried out under pressure.

Filtration of the reaction mixture is then carried out at a temperature >50° C., advantageously at the same temperature as the reaction temperature, preferably from 60° to 100° C., depending on the boiling point of the solvent. The filtration is effected at a temperature above 50° C. at which 1-naphthol-4-sulphonic acid has a solubility of 0.01–5% by weight in the specific solvent utilized. The resulting filter cake is preferably washed with pure solvent, preferably at a temperature close to the filtration temperature. Alternatively or in addition, a washing step may be carried out with a solvent of lower boiling point, but in which the solubility of the product is similar to that in the reaction medium.

The resulting filter cake contains 1-naphthol-4-sulphonic acid in the free acid form, contaminated by a very low content of the undesired 2-isomer and of further organic impurities. The content of 1-naphthol-2-sulphonic acid in the final product is lower than 2% by weight, and can be as low as 0.5% by weight or even lower, based on the weight of 1-naphthol-4-sulphonic acid. Further organic impurities which may be present are 1-naphthol in an amount of 0.5% by weight or even less and 1-naphthol-2,4-disulphonic acid in an amount from 1 to 3% by weight, all based on the weight of the NW acid.

After filtration and removal of the mother liquor by washing, the resulting filter cake may be dried, conveniently at a temperature below 120° C., optionally under vacuum.

Before drying, the filter cake may be further washed or stirred with the same solvent as the sulphonation solvent or a different solvent and then filtered at the same temperature conditions as indicated above. If another solvent is used, it may not be fully inert towards the sulphonating agent but it should have solubilising properties similar to those of the sulphonation solvent. Examples of such solvents are alkyl $C_{1-6}$-aryl ethers such as anisol or phenetol. The amount of solvent used for this treatment generally ranges from 2 to 20 times the volume of the filter cake.

Contrary to what has hitherto been believed, the method of the invention enables the production of 1-naphthol-4-sulphonic acid in the free acid form by direct separation from the reaction mixture after completion of sulphonation.

Instead of being dried, the filter cake can be dissolved in water and the organic solvent is removed according to known methods. The resulting aqueous solution of 1-naphthol-4-sulphonic acid is ready for use. If desired, the free acid can also be converted into the salt form according to known methods. For example, the sodium sulphonate can be obtained by addition of sodium chloride to the aqueous solution and subsequent washing of the filter cake with brine. The resulting sodium 1-naphthol-4-sulphonate is practically in the pure form.

The entire specification of parent application Ser. No. 597,172, particularly pages 1–5, is hereby incorporated as if it were set forth herein in its entirety.

The following Examples, in which all temperatures are in degrees Centigrade, illustrate the invention.

EXAMPLE 1

73 g 1-Naphthol are introduced in 500 ml chlorobenzene at 30°. 60 g Chlorosulphonic acid are then added dropwise and the reaction is continued at 80° for 4 hours. After this period the reaction mixture contains 1-naphthol-4-sulphonic acid and 5% by weight based on the theoretical yield of 1-naphthol-2-sulphonic acid.

The reaction mixture is filtered and the filter cake is rinsed with 400 ml hot chlorobenzene to remove the remaining mother liquor. After drying under vacuum, the resulting filter cake contains 1-naphthol-4-sulphonic acid in a yield of 92% of theory and <0.5% 1-naphthol-2-sulphonic acid and 3% of 1-naphthol-2,4-disulphonic acid based on the weight of 1-naphthol-4-sulphonic acid.

The chlorobenzene wet filter cake can be introduced in 200 ml water with stirring. After elimination of the solvent, there is obtained an aqueous solution which after clarification is ready for use.

According to another alternative, 60 g sodium chloride can be added to the resulting aqueous solution. The precipitated sodium 1-naphthol-4-sulphonate is filtered and washed with brine. Sodium 1-naphthol-4-sulphonate substantially free from organic impurities is thus obtained in a theoretical yield of 88%.

EXAMPLE 2

By following the reaction procedure of Example 1 but using 1,2-dichlorobenzene instead of chlorobenzene, a reaction mixture containing 4% of the theoretical yield of 1-naphthol-2-sulphonic acid is obtained.

By treating the reaction mixture as disclosed in Example 1, free 1-naphthol-4-sulphonic acid is obtained in a theoretical yield of 93%. It contains <0.5% 1-naphthol-2-sulphonic acid and 2% 1-naphthol-2,4-disulphonic acid based on its weight.

EXAMPLE 3

73 g 1-Naphthol and 60 g chlorosulphonic acid are reacted in 500 ml of a mixture of trichlorobenzene isomers according to the procedure of Example 1. The resulting reaction mixture contains 2% of the theoretical yield of 1-naphthol-2-sulphonic acid. After filtration and rinsing with 400 ml hot trichlorobenzene, the filtrate is taken up in 300 ml water and the solvent is removed. The resulting aqueous solution contains 1-naphthol-4-sulphonic acid in a theoretical yield of 93%, and 0.5% 1-naphthol-2-sulphonic acid and 3% 1-naphthol-2,4-disulphonic acid based on the weight of the NW acid.

EXAMPLE 4

The procedure of Example 3 is repeated except that the filter cake is rinsed with 400 ml hot chloroform instead of the trichlorobenzene to remove the mother liquor from the filter cake.

After drying, a filter cake is obtained which contains free 1-naphthol-4-sulphonic acid with a theoretical yield of 92% and <0.5% 1-naphthol-2-sulphonic acid and 1% 1-naphthol-2,4-disulphonic acid based on the weight of the 4-sulphonic acid.

EXAMPLE 5

73 g 1-Naphthol are reacted at 0° in 700 ml toluene with 61 g chlorosulphonic acid added dropwise. The sulphonation reaction is then continued at 80° for 4 hours. The resulting reaction mixture contains 5% of the theoretical yield of 1-naphthol-2-sulphonic acid. The reaction mixture is then filtered and the mother liquor is removed from the filter cake by rinsing with 500 ml hot toluene.

By treating the filter cake as disclosed in Example 1, free 1-naphthol-4-sulphonic acid is obtained in a theoretical yield of 88% and containing 0.5% 1-naphthol-2-sulphonic acid and 1-naphthol and 2% 1-naphthol-2,4- disulphonic acid based on the weight of the NW acid. After conversion into the salt form as disclosed in Example 1, sodium 1-naphthol-4-sulphonate substantially free from organic impurities is obtained in a 85% theoretical yield.

EXAMPLE 6

73 g 1-Naphthol and 60 g chlorosulphonic acid are reacted in 700 ml benzene according to the procedure of Example 5. The resulting reaction mixture contains 7% 1-naphthol-2-sulphonic acid.

By treating the reaction mixture as disclosed in Example 1, free 1-naphthol-4-sulphonic acid containing 1% 1-naphthol-2-sulphonic acid and 3% 1-naphthol-2,4-disulphonic acid based on its weight is obtained in a 87% yield.

EXAMPLE 7

73 g 1-Naphthol and 65 g chlorosulphonic acid are reacted in 700 ml isomeric xylene mixture according to the procedure of Example 5. The resulting reaction mixture contains 2% 1-naphthol-2-sulphonic acid.

By treating the reaction mixture as disclosed in Example 1, free 1-naphthol-4-sulphonic acid is obtained in 80% yield. It contains <0.5% 1-naphthol-2-sulphonic acid and 0.5% 1-naphthol-2,4-disulphonic acid based on the weight of the NW acid.

EXAMPLE 8

73 g 1-Naphthol are reacted at 50° in 300 ml 1,1,2-trichloroethane with 60 g chlorosulphonic acid added dropwise. The sulphonation reaction is continued at 80° for a further 4 hour period. The resulting mixture contains 7% 1-naphthol-2-sulphonic acid. After filtration of the reaction mixture, the filter cake is rinsed with 300 ml 1,1,2-trichloroethane to remove the mother liquor from the filter cake.

After drying, free 1-naphthol-4-sulphonic acid is obtained in 80% yield. It contains 1% 1-naphthol-2-sulphonic acid and 1% 1-naphthol-2,4-disulphonic acid based on the weight of the NW acid.

EXAMPLE 9

73 g 1-Naphthol and 60 g chlorosulphonic acid are reacted at 50° in 800 ml 1,1,2,2-tetrachloroethane and the reaction is continued at 80° for 4 hours. The resulting reaction mixture contains 4% of the theoretical yield of 1-naphthol-2-sulphonic acid. After filtration of the reaction mixture, the filter cake is rinsed with 500 ml 1,1,2,2-tetrachloroethane to remove the mother liquor from the filter cake.

After drying, free 1-naphthol-4-sulphonic acid with a content of <0.5% 1-naphthol-2-sulphonic acid and 2% 1-naphthol-2,4-disulphonic acid, is obtained in a theoretical yield of 90%.

EXAMPLE 10

73 g 1-Naphthol and 65 g chlorosulphonic acid are reacted at 60° at the boil in 600 ml chloroform, and further stirred at 60° for 10 hours to give a mixture containing 10% 1-naphthol-2-sulphonic acid.

The resulting reaction mixture is filtered and the filter cake is rinsed with 500 ml chloroform to be freed from the mother liquor. After drying, a filter cake containing free 1-naphthol-4-sulphonic acid in 80% yield, 0.5% 1-naphthol-2-sulphonic acid and <0.5% 1-naphthol-2,4-disulphonic acid (based on the NW acid weight) is obtained.

EXAMPLE 11

73 g 1-Naphthol and 60 g chlorosulphonic acid are reacted at the boil in 500 ml trichloroethylene and are further stirred at the boil for 2 hours, giving a product containing 3% 1-naphthol-2-sulphonic acid. After filtration of the reaction mixture, the filter cake is washed with 300 ml trichloroethylene to be freed from the mother liquor. The content of 1-naphthol-2-sulphonic acid in the filter cake is approx. 2% of the theoretical yield.

The filter cake is further purified by a treatment at the boil in 500 ml trichloroethylene followed by filtration. After drying, free 1-naphthol-4-sulphonic acid is obtained in a yield of 90%. It contains 1% 1-naphthol-2-sulphonic acid and 3% 1-naphthol-2,4-disulphonic acid (based on the NW acid weight).

EXAMPLE 12

The procedure of Example 11 is repeated but the filter cake is further purified by a treatment with anisol followed by filtration. After drying, free 1-naphthol-4-sulphonic acid is obtained in a yield of 89%. It contains <0.5% 1-naphthol-2-sulphonic acid and 3% 1-naphthol-2,4-disulphonic acid (based on the NW acid weight).

In Example 6 the filtration was effected at approximately 70° C., in Example 10 the filtration was effected at approximately 60° C., and in each of the other examples the filtration was effected at approximately 80° C.

What is claimed is:

1. A method for producing 1-naphthol-4-sulphonic acid in free acid form contaminated with less than 2% by weight of 1-naphthol-2-sulphonic acid, by sulphonating 1-naphthol in a solvent which is substantially inert towards the sulphonating agent and in which 1-naphthol-4-sulphonic acid has a solubility at a temperature >50° C. of from 0.01 to 5.0% by weight, which comprises the step of separating the 1-naphthol-4-sulphonic acid from the reaction mixture by filtration at a temperature >50° C. directly after completion of the sulphonation.

2. A method according to claim 1, in which the solvent is selected from halogenated aliphatic hydrocarbons and aromatic monocyclic hydrocarbons which are optionally nitrated or halogenated.

3. A method according to claim 1, in which the solvent is selected from benzene, toluene, xylene, nitrobenzene, nitrotoluene, monochlorobenzene, dichlorobenzenes, trichlorobenzenes, chloroform, trichloroethylene, 1,1,1- or 1,1,2-trichloroethane, tetrachloroethylene or 1,1,2,2-tetrachloroethane.

4. A method according to claim 1 in which the solvent is used in an amount from 2 to 20 times the amount of 1-naphthol.

5. A method according to claim 1, in which the sulphonating agent is chlorosulphonic acid.

6. A method according to claim 5, in which chlorosulphonic acid is added at a temperature from −20° to +20° C. in an excess from 5 to 20% by weight when the solvent is an aromatic monocyclic hydrocarbon.

7. A method according to claim 5, in which chlorosulphonic acid is added at a temperature >20° C. in a stoichiometric amount or in an excess up to 5% by weight when the solvent is an halogenated or nitrated hydrocarbon.

8. A method according to claim 1, in which the reaction mixture is heated at a temperature >50° C. after addition of the sulphonating agent.

9. A method according to claim 1, in which the reaction mixture is heated at a temperature from 60° to 100° C. after addition of the sulphonating agent.

10. A method according to claim 1, in which filtration of the reaction mixture is carried out at the same temperature at the reaction.

11. A method according to claim 1, in which filtration is carried out at a temperature from 60° to 100° C.

12. A method according to claim 1 in which the content of 1-naphthol-2-sulphonic acid in the final product is up to 0.5% by weight based on the weight of 1-naphthol-4-sulphonic acid.

13. A method according to claim 8 in which filtration of the reaction mixture is carried out at the same temperature as the reaction.

14. A method according to claim 9 in which filtration of the reaction mixture is carried out at a temperature of 60°–100° C.

15. A method according to claim 9 in which filtration of the reaction mixture is carried out at the same temperature as the reaction.

16. A method according to claim 13 in which the amount of solvent is 2 to 20 times the amount of 1-naphthol by weight.

17. A method according to claim 14 in which the amount of solvent is 2 to 20 times the amount of 1-naphthol by weight.

18. A method according to claim 14 in which the solvent is selected from the group consisting of benzene, toluene, xylene, nitrobenzene, nitrotoluene, monochlorobenzene, dichlorobenzene, trichlorobenzene, chloroform, trichloroethylene, 1,1,1- and 1,1,2-trichloroethane, tetrachloroethylene and 1,1,2,2-tetrachloroethane.

19. A method according to claim 14 in which the sulphonating agent is chlorosulphonic acid.

20. A method for producing 1-naphthol-4-sulphonic acid in free acid form contaminated with less than 2% by weight of 1-naphthol-2-sulphonic acid which comprises dissolving 1-naphthol in a solvent selected from the group consisting of aromatic monocyclic hydrocarbons, which may be nitrated or halogenated, and halogenated aliphatic hydrocarbons and in which 1-naphthol-4-sulphonic acid has a solubility of from 0.01 to 5.0%, by weight, at a temperature >50° C., adding chlorosulphonic acid to the dissolved 1-naphthol in an amount ranging from stoichiometric to 20%, by weight, in excess of stoichiometric and at a temperature of −20° to 120° C., heating the resulting reaction mixture for 1–12 hours at a temperature >50° C. after completing addition of the chlorosulphonic acid and, directly thereafter, filtering the reaction mixture at a temperature >50° C. at which 1-naphthol-4-sulphonic acid has the said solubility in said solvent.

* * * * *